United States Patent [19]

Meyer-Ebrecht et al.

[11] 4,075,484
[45] Feb. 21, 1978

[54] DEVICE FOR MEASURING RADIATION ABSORPTION OR EMISSION

[75] Inventors: Dietrich Meyer-Ebrecht; Günter Kowalski, both of Hamburg, Germany

[73] Assignee: U.S. Philips Corporation, New York, N.Y.

[21] Appl. No.: 705,051

[22] Filed: July 14, 1976

[30] Foreign Application Priority Data

July 15, 1975 Germany .............................. 2531477

[51] Int. Cl.² .............................................. G01T 1/20
[52] U.S. Cl. .................................. 250/366; 250/360; 250/445 T
[58] Field of Search ..................... 250/366, 445 T, 360

[56] References Cited

U.S. PATENT DOCUMENTS

| | | | |
|---|---|---|---|
| 2,512,355 | 6/1950 | Marshall | 250/358 R |
| 2,539,203 | 1/1951 | Pohl | 250/354 |
| 2,653,247 | 9/1953 | Lundahl | 250/354 |
| 3,417,244 | 12/1968 | Kramer | 250/358 R |
| 3,944,830 | 3/1976 | Dissing | 250/358 R |

Primary Examiner—Harold A. Dixon
Attorney, Agent, or Firm—Frank T. Trifari

[57] ABSTRACT

A device for correcting measuring values of a group of radiation detectors for measuring the intensity or distribution of radiation, comprising an additional radiation source for direct irradiation of the detectors. The radiation of the said additional radiation source can be switched on each time when the radiation to be measured is not incident on the radiation detectors. The device furthermore comprises a calculating device which forms for each radiation detector the quotient of the measuring value (M1(x)) and the reference measuring value (M2(x)) of the radiaton detectors when exposed to the radiation of the additional radiation source.

13 Claims, 5 Drawing Figures

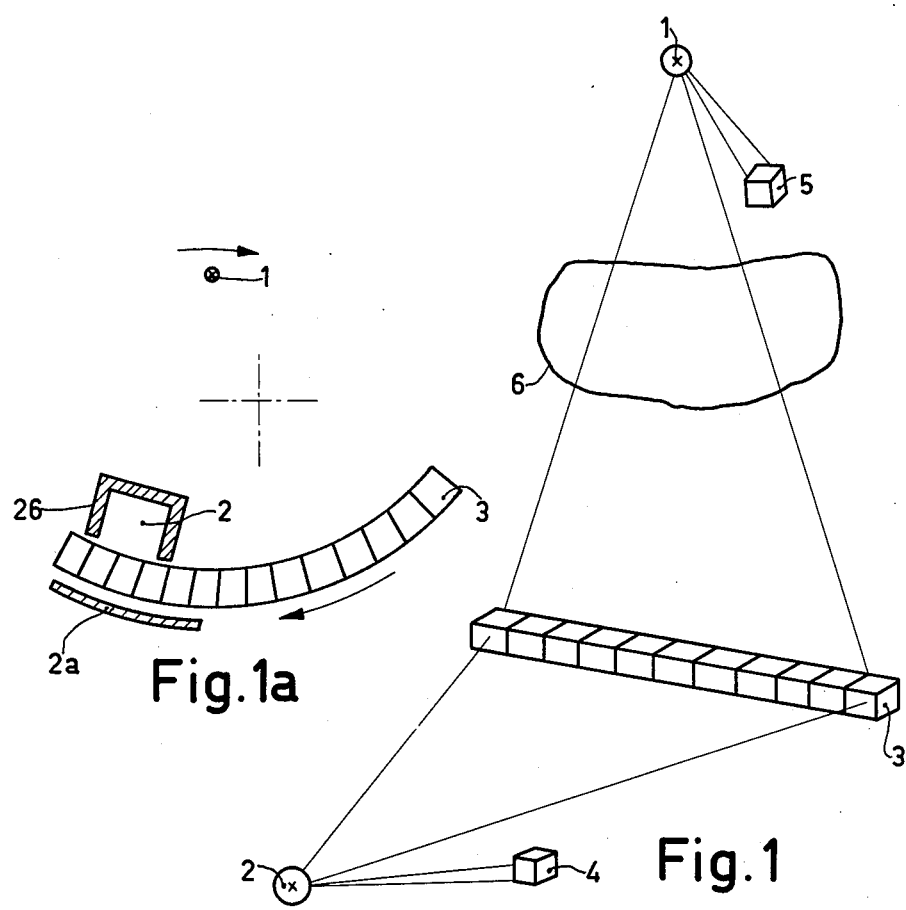
Fig.1a
Fig.1
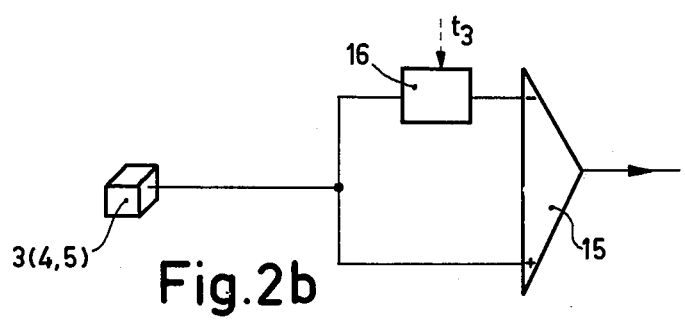
Fig.2b

DEVICE FOR MEASURING RADIATION ABSORPTION OR EMISSION

The invention relates to a device for correcting the measuring values of a group of radiation detectors which measure the intensity of radiation passing through an object or generated by an object.

A device of this kind is known, for example, from German Offenlegungsschrift, No. 1,941,433. In an apparatus described therein, a radiator, whose radiation passes through the body to be examined and is measured by the radiation detectors, is rotated around the body together with the radiation detectors, so that the radiation absorption of the body can be measured in planes of different orientation. The spatial distribution of the absorption in the body can be determined on the basis of the measuring values thus obtained by employing suitable calculating methods.

The accuracy of the absorption distribution thus obtained is substantially dependent of the fact whether or not the measuring values are influenced by changes in the properties of the parts used. The known device includes a reference detector which is exposed to radiation which has not passed through the body to be examined. When the measuring values produced by the detectors are related to the output signal of the reference detector (i.e. divided thereby), a value is obtained which is independent of fluctuations in the intensity of the X-ray radiator.

However, the influence of the fluctuations of the radiation intensity of the radiator is exceeded in practice by the fact that the sensitivity of the radiation detectors relative to each other is not equally high and is subject to fluctuations in the time. The accuracy of the results obtained by means of this device is thus adversely affected.

The invention has for its object to provide a device of the kind set forth in which values are obtained which are dependent of the absorption or the emission of the body to be examined, but not of fluctuations or irregularities of the detector properties. To this end, an apparatus of the kind set forth in accordance with the invention is characterized in that there is provided an additional radiation source for direct exposure of the radiation detectors, it being possible to switch on the radiation of the additional source when the radiation to be measured is not incident on the radiation detectors, there also being provided a calculating device which forms for each radiation detector the quotient of a measuring value and a reference measuring value of the radiation detector when exposed to the radiation of the additional radiation source.

One embodiment of the device in accordance with the invention will be described in detail hereinafter with reference to the diagrammatic drawing.

FIGS. 1 and 1a diagrammatically shows the construction of a device in accordance with the invention.

FIGS. 2a and 2b is a circuit diagram for analog signal processing.

Figure 2A:
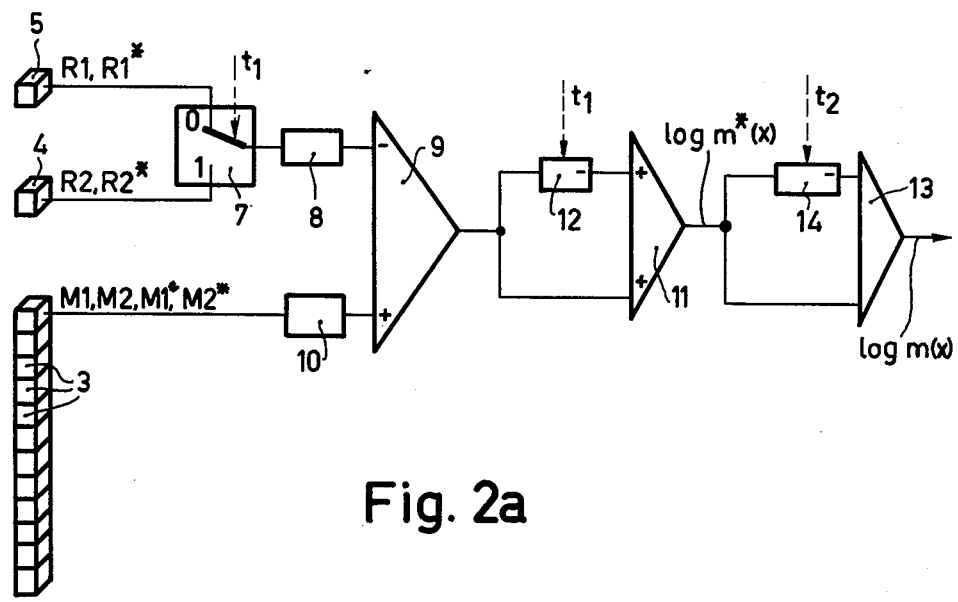

The drawing diagrammatically shows a radiation source 1, for example, an X-ray radiator whose beam is stopped to form a flared, narrow beam in a direction perpendicular to the plane of the drawing; this beam passes through a body 6 and is incident on a group of radiation detectors arranged behind the body 6. The measuring value produced by each radiation detector is dependent of the absorption of the part of the body 6 situated between the radiation source 1 and the relevant radiation detector.

When the radiation source 1 does not emit a beam, an additional radiation source 2 is briefly switched on, the radiation of the said additional source being directly incident on the detectors 3 without passing through the body 6. If it is assumed that the sensitivity of a radiation detector does not change during the period during which a radiation detector is exposed to the radiation of the radiation source 1 (attenuated by the body 6) and to the radiation of the additional radiation source 2, the measuring value M1 $(x)$, measured during exposure to the radiation source 1, as well as the measuring value M2$(x)$, measured by the radiation detector when exposed to the radiation source 2, are dependent of the sensitivity of the relevant radiation detector to the same extent; $x$ is a location co-ordinate which each time characterizes the individual radiation detector 3 within the group. Therefore, the quotient $$m(x) = M1(x) / M2(x) \qquad (1)$$

is a value which is independent of the sensitivity of the relevant radiation detector and which is dependent only of the absorption of the part of the body which is situated between the radiation detector and the radiation source 1. For the additional radiation source use is preferably made of a radioactive isotope whose spectral distribution at least approximates that of the radiation source 1 and which has an adequate half-life value. This is because isotopes are very stable, so that always reproducible relationships are obtained. In order to enable the use of an isotope which emits as little radiation as possible, it would have to be arranged in the immediate vicinity of the detectors 3. For example, use can be made of a spatially small isotope which each time irradiates one radiation detector, means being provided which shift the isotope 2 and the group of radiation detectors 3 relative to each other, so that the radiation detectors are successively exposed to the radiation of the isotope 2, for example, as diagrammatically shown in FIG. 1a for a group of detectors which are arranged on an arc of a circle and which rotate about a centre. The isotope 2 is shielded by apertures 2a, 2b so that its radiation cannot escape to the surroundings.

However, in the case of radiation detectors which consist of a combination of a scintillator crystal and a photomultiplier, for example, an additional radiation source 2 having a spectral range other than the radiation source 1 can be chosen. For the calibration of notably the photomultipliers it is advantageous to choose the spectrum of the radiation source 2 in the visible range, i.e. approximately corresponding to the spectral range of the light emitted by the scintillators. It is then possible to guide the radiation of the radiation source 2 to the radiation detectors by way of light conductors, so that a particularly simple and space-saving mechanical construction is realized.

In practice, however, notably the radiation source 1 and possibly also the radiation source 2 do not have the required stability in the time, so that the fluctuations in the radiation intensity could influence the measuring result. However, this measuring error can be avoided by arranging at least one reference radiation detector (4, 5) in front of one of the radiation sources, the said reference radiation detector being exposed directly to the radiation of additional radiation source (2) or to the radiation to be measured, an output signal (R2, R1) of the reference detector (4,5) being used as a reference quantity for the measuring values (M2(x), M1(x)) of the radiation detectors during exposure to the radiation of the additional radiation source (2) or to the radiation to be measured.

A reference detector is thus associated with each radiation source whose intensity may be subject to fluctuations in the time. In FIG. 1, the reference detector 5 is associated with the radiation source 1 and a reference detector 4 is associated with the radiation source 2, the latter detector being exposed only to the radiation of the added radiation source, A body having a defined absorption can also be arranged between the radiation source and the radiation detector 5, the said absorption corresponding approximately to be anticipated absorption of the body 6, as is known from German Offenlegungsschrift No. 1.941.433. However, it is important that the radiation incident on the reference detector 5 is not attenuated by the body 6 to be examined.

When the output signal of the two reference detectors is taken as the reference quantity for the output signals of the radiation detectors when exposed to the radiation source each time assigned, the formula (1) becomes $$m(x) = \frac{M1(x)}{M2(x)} \cdot \frac{R2}{R1} \quad (2)$$

Therein, R1 is the output signal of the reference detector 5 associated with the radiation source 1, and R2 is the output signal of the reference detector 4 associated with the radiation source 2. Because the values M1(x)·R2 and M2(x)·R1 change to the same extent when the intensity of the radiator 1 or 2 changes, the value $m(x)$ is independent of the fluctuations of the intensity of the two radiators. The reference detectors 4 and 5 in this device, however, would have to specially stabilized in order to prevent influencing of the measuring result by a change in sensitivity of the reference detectors.

A further measuring error may occur in that the share of the radiation source 1 and/or the additional radiation source 2 is not the same for each radiation detector, for example, if the radiation detectors are not arranged in an arc of a circle around the radiation sources, or if the radiation sources emit radiation with a different intensity in various directions. This measuring error can be avoided by means of a calculating circuit (7 . . . 14, 18 . . . 31), in the case of exposure to the first and/or additional radiation source, divides the measuring values (M1(x), M2(x)) of the radiation detectors (3) by the output signals (M1*(x), M2*(x)) of the same radiation detectors when exposed each time to the same radiation source, however, without the body to be examined being present in the beam path of the first radiation source.

The formula (2) then becomes $$m(x) = \frac{M1(x)}{M2(x)} \cdot \frac{R2}{R1} \cdot \frac{1}{m^*(x)} \; ; \; m^*(x) = \frac{M1^*(x)}{M2^*(x)} \cdot \frac{R2^*}{R1^*} \quad (3)$$

Therein, all quantities denoted by an asterisk are measuring values measured directly prior to the introduction in or directly after the removal of the body from the direct beam path between logarithmic amplifiers, a multiplication (for example, M1/R1]R2/M2) being effected by addition of the output signals (log M1/R1+log R2/M2) of the logarithmic amplifiers.

Figure 3:
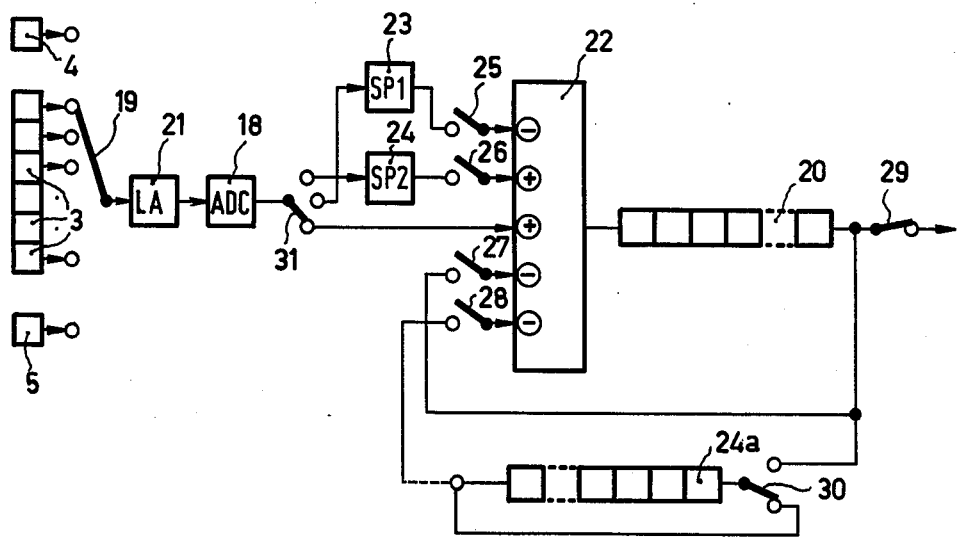
FIG. 3 shows a circuit arrangement for the digital processing of measuring values.

Use is made of the fact that the measuring value M1(x) is exponentially dependent of the absorption coefficient or the density of the object, so that for the measurement of the absorption coefficient or the density in the plane, the logarithm of the measuring value must be calculated anyway. Multiplications and divisions are thus converted into an addition and a subtraction, respectively, of the logarithmically calculated measuring values which can be realized quickly and inexpensively. FIGS. 2a and 3 show calculating circuits which are suitable for calculating the formula (3), the said circuits operating on an analog (FIG. 2a) and a digital basis (FIG. 3), respectively.

In the circuit shown in FIG. 2a, the outputs of the reference detectors 4 and 5 are connected to the input of a logarithmic amplifier 8 via a switch 7. The switch 7, controlled by the clock pulse signal $t_1$, is always in the position shown, in which it connects the reference detector 5 to the logarithmic amplifier 8, when the radiation source 2 is not active. The output signals of each radiation detector are applied to the positive input of a superposition circuit 9 via a logarithmic amplifier 10. The output signal of the logarithmic amplifier 8 is present on a negative input of the superposition circuit 9. The output of the superposition circuit 9 is connected to both positive inputs of an adding circuit 11, i.e. directly to one input and to the other input via an intermediate store 12, which is assumed to reverse the sign of the signal and which is controlled by the clock pulse signal $t_1$ so as to store a new input value.

For the intermediate store, use can be made of a sample-and-hold store or of a unit which averages the signal for the period during which one of the sources emits radiation. These stores can be realized, for example, by integrators which integrate the values present during the period in which the relevant radiation source emits radiation. However, in that case additional clock pulse signals are required for resetting the integrators prior to the taking over of a new value.

The output of the adding circuit 11 is connected to the two positive inputs of a further adding circuit 13, again once directly and once via an intermediate store 14 which is also assumed to reverse the polarity of the signal stored.

The calculating circuit shown in FIG. 2a forms, in combination with the device shown in FIG. 1, the value $m(x)$ according to the formula (3) in four phases.

During the first phase, during which the body to be examined is not present in the beam path, the additional radiation source 2 is switched on. The signal log M2* then appears on the output of the logarithmic amplifier 10, and the signal log R2* appears on the output of the logarithmation amplifier 8. Consequently, the value log M2* − log R2* is obtained on the output of the superposition circuit 9, the said value being stored in the intermediate store 12 under the control of the clock pulse signal $t_1$.

During the second phase, the radiation source 1 is switched on and the body to be examined is still not present in the beam path; the signals R1* and M1* are then formed, the said signals being combined on the output of the superposition circuit 9 so as to form log M1* − R1*. This value is added to the inverted value of the first calculating phase stored in the intermediate store 12 by the adding circuit 11, with the result that on the output of the adding circuit 11 the quantity log M1*

$-\log R1^* - \log M2^* + \log R2^* = \log M1^* R2^*/M2^* R1^* = \log m^*(x)$.

This value is stored, under the control of the signal $t_2$, in the intermediate store 14 in which its polarity is reversed.

During the third calculating phase, the body to be examined is present in the beam path and the additional radiation source 2 is switched on. On the output of the superposition circuit 9 the values log M2 − log R2 are obtained; these values are stored, under the control of the clock pulse signal $t_1$, in the intermediate store 12, in which their sign is reversed.

Finally, during the fourth calculating phase the radiation source 1 is switched on; this source irradiates the body to be examined, a signal which is proportional to the quantity log M1 − R1 then appearing on the output of the adding circuit 9. This signal is added to the contents of the intermediate store 12 by adding circuit 11, so that the quantity log M1 − log R1 − log M2 + log R2 = log M1 R2/M2 R1 is obtained on the output of the circuit 11. The quantity log $m^*$ is subtracted therefrom by the components 13 and 14, so that the signal log $m$ appears on the output of the adding circuit 13.

The measurement of the signals M1*, M2, M2*, R1*, R2, R2* need not be repeated for each measuring value (M1) measured by the detectors, so that the fourth phase can alternatively consist of the recording of a whole group of measuring values or of the derivation of a continuous signal (German Patent Application No. P 25 03 789.2).

The circuit can also be elaborated so that the superposition and adding circuits 9, 11 and 13 can be dispensed with. To this end, the output signal of the logarithmic amplifier must be converted into a proportional current by a resistor, and the same must be done with the output signal of the logarithmic amplifier 8 whose polarity must also be reversed by a phase reversing circuit. The two resistors are combined, so that a signal which is proportional to the difference of the logarithms of two quantities is obtained at their junction. The junction is connected, via a switch which replaces the superposition circuit 9 and which is controlled by the clock pulse signal $t_1$, either to the input of the intermediate store 12 or directly to a further summing point which is connected to the output of the intermediate store 12 via a further resistor. This further summing point is connected, via a second switch, either to the input of the intermediate store 14 or directly to a third summing point which at the same time serves as the output of the circuit and whereto the output of the intermediate store 14 is connected via a resistor which converts the output signal of the intermediate store into a proportional current.

FIG. 2a shows only a single calculating circuit.

Actually, a calculating circuit of this kind is associated with each radiation detector, the components 7 and 8 being provided only once because they operate in common for all circuits. These components could be dispensed with by connecting the radiation detectors successively to the input of the logarithmic amplifier 10 via a control switch. In that case, however, only a comparatively short period of time would remain for performing the calculation, so that the accuracy would be adversely affected. If it is not necessary to use reference detectors, either because their sources are sufficiently stable or because the deviation of the source intensity does not cause a significant error, because all detector measuring values mutually deviate by the same amount, the revelant circuit elements, i.e. 7, 8 and 9, can be dispensed with.

In practice a measuring error is also caused by the unavoidable dark currents of the radiation or reference detectors. The measuring error caused by the dark currents can be avoided by intermediately storing the output signals of the radiation detectors (3) and the reference detectors (4, 5) produced during the radiation interval, prior to the conversion to logarithms, each time in a store (16), a subtraction circuit (15) being provided which subtracts the stored values from the measuring values (M1, M2, R1, R2 ...) of the radiation detectors and the reference detectors. As is shown in FIG. 2b, the output signals of the radiation detectors 3 and the reference detectors 4 and 5 are each time stored in a store 16 prior to the conversion to logarithms for the period of time during which the detectors are not irradiated. This stored dark current value is subtracted each time from the values M1, M2, R1, ... in the adding circuit 15.

FIG. 3 shows the block diagram of a digital calculating circuit which forms the value $m(x)$, and which operates in series. The required digitalization is effected by means of a single analog-to-digital converter 18 which successively takes up the output signals of the detectors 3 and possibly those of the reference detectors 4 and 5 via a multiplex switch 19. The values which are produced as a temporary series of binary values by the analog-to-digital convertor can be stored in a shift register 20, the number of cells of which corresponds to the number of radiation detectors, each cell being capable of storing a detector output signal in a number of binary positions which corresponds to the processing accuracy. The conversion to logarithms of the separate output signals is preferably again effected in a logarithmic amplifier 21 preceding the analog-to-digital convertor.

The essential part of the calculating circuit is a superposition member 22 comprising two add inputs (+) and three subtract inputs (−), and also comprising two digital storage cells 23 and 24 for the intermediate storage of the quantities log R1 and log R2, respectively, and, if necessary, a further shift register 24 for the intermediate storage of the quantity log $m^*(x)$. A control logic system (not further shown) controls the information flow via a series of gate circuits which are in this case represented by the switches 25 to 29 and the switches 30 to 31.

The calculating circuit operates as follows: After a radiation pulse from the additional radiation source 2, the values M2(x) of all radiation detectors 3 and also the value R2 of the reference detector 4 are consecutively read via the multiplex switch 19. The values whose logarithm has been formed and the digitalized values log M2(x) are stored directly in the shift register 20 (the other information inputs of the superposition member 22 are blocked during this time), log R2 being stored in the intermediate store 24. Subsequently, the actual measurement takes place, i.e. a radiation pulse from the radiation source 1. First the output signals of the reference detector 5 and then the measuring values M1(x) of the radiation detectors are consecutively read. The value log R1 is stored in the store 23. The individual values log M1(x) are combined, after through-connection of all signal inputs in the superposition circuit 22, with the contents of the corresponding storage elements in accordance with the formula:

$$m(x) = \log M1(x) - \log M2(x) + \log R2 - \log R1 - \log m^*(x).$$

The output values log $m(x)$ are shifted into the shift register 20, whilst at the same time the previously stored values log $M2(x)$ are shifted out of the shift register 20, so that they are available for the calculating operation. Simultaneously, the correction values Log $m^*(x)$ are shifted out of the shift register 24a. After completion of this procedure, the corrected values log $m(x)$ are available in the shift register 20.

The correction values log $m^*(x)$ are obtained by performing the described procedure without the body to be examined being present in the beam path. The output of the shift register 24a, however, is not connected to the superposition member 22 (the switch 28 is open). The result of this measurement is log $m^*(x)$. These values are subsequently shifted from the register 20 into the shift register 24a. During the subsequent calculations of the values log $m(x)$, log $m^*(x)$ is retained in the store 24, the input of the shift register 24a therein being connected to the output thereof.

The shift register 24a, the switch 28 and the switch 30 can be dispensed with if a corresponding correction is not required, i.e. if the output signal of a radiation detector is independent of its position in the radiation detector group. If the relationships do not change in the time, the shift register 24 can also be replaced by a read-only memory.

If no reference detectors are required, the circuit elements 23, 24, 25 and 26 and two inputs of the superposition unit can be dispensed with.

What is claimed is:

1. In a measuring system including a main source of radiation and a plurality of radiation detectors positioned to receive radiation from said main source, wherein the passage of radiation from said main source to said detectors may be interrupted; the improvement comprising a second source of radiation, means for irradiating said detectors with radiation of said second source when radiation from said main source is not incident thereupon, and circuit means connected to produce the quotient $M_1/M_2$ for each of said detectors, wherein $M_1$ is a measuring value of the related detector due to irradiation from said main source and $M_2$ is a measuring value of the relevant detector due to irradiation from said second source in the absence of incident radiation from said first source.

2. The measuring system of claim 1, wherein said second source comprises a radioactive isotope, said isotope and radiation detectors being movable relative to each other.

3. The system of claim 1, in which said radiation detectors are comprised of photomultipliers and scintillator crystals, said second radiation source comprising a light source directed toward said photomultipliers.

4. The system of claim 1, further comprising a reference radiation detector positioned to receive radiation from at least one of said sources, for producing a reference value for the radiation of the respective source.

5. The measuring system of claim 1, further comprising reference radiation detecting means positioned to be exposed directly to the radiation of said source for producing reference quantities for the measuring values of said plurality of radiation detectors.

6. The system of claim 1, for measuring radiation passing through an object, wherein radiation may be received at times by said radiation detectors which does not pass through said object, wherein said circuit means comprises means for dividing at least one of said measuring values $M_1$ and $M_2$ when said radiation passes through said object by the corresponding value when said radiation does not pass through said object.

7. The system of claim 1, wherein said circuit means comprises logarithmic amplifier means connected to said detectors, and subtraction circuit means connected to said amplifiers for producing said quotient.

8. The system of claim 1, further comprising reference detectors connected to directly receive radiation from each of said sources, to provide reference measuring values for the respective sources.

9. The system of claim 8, further comprising logarithmic amplifier means connected to said detectors, and subtraction and addition circuit means connected to form an output signal (log $M_1/R_1$ + log $GR_2/M_2$).

10. The system of claim 9, further comprising intermediate storage means connected to store signals prior to the application of signals to said logarithmic amplifiers.

11. The system of claim 1, for determining radiation absorbed by an object, wherein said plurality of detectors may be relatively movable to receive radiation directly from said main source and radiation that passes through said object from said main source, said system further comprising further detector means for receiving radiation directly from said sources to produce reference measuring values $R_1$ and $R_2$ corresponding to the radiation of said main and second sources, respectively, said circuit means further comprising means for converting the outputs of said detectors to logarithmic equivalents of the radiation received thereby, and means for subtracting said logarithmic equivalents to produce signals corresponding to the logarithms of the outputs of the reference detectors and the outputs of the corresponding plurality of detectors.

12. The system of claim 11, wherein said circuit means further comprises first and second adding means, first and second intermediate storage means, means applying the outputs of said subtracting means to said first adding means directly and by way of said first storage means to said first adding means, and means applying the output of said first adding means directly and by way of said second intermediate storage means to said second adding means, and further comprising clock means for controlling said storage means, whereby the output of said second adding means corresponds to the antilog of $M_1 R_2/M_2 R_1 m^*$, wherein $m^*$ is a measuring value in the absence of said object.

13. The system of claim 1, wherein said circuit means comprises analog to digital conversion means for converting the outputs of said detectors to digital form, and digital circuit means for producing said quotient.

* * * * *

UNITED STATES PATENT AND TRADEMARK OFFICE
CERTIFICATE OF CORRECTION

PATENT NO. : 4,075,484
DATED : February 21, 1978
INVENTOR(S) : DIETRICH MEYER-EBRECHT ET AL It is certified that error appears in the above-identified patent and that said Letters Patent are hereby corrected as shown below:

Column 2, line 46, "2a, 2b" should be --2a and 2b--

Signed and Sealed this

Twentieth Day of June 1978

[SEAL]

Attest:

RUTH C. MASON
Attesting Officer

DONALD W. BANNER
Commissioner of Patents and Trademarks